US005677423A

United States Patent [19]
Rodriguez

[11] Patent Number: 5,677,423
[45] Date of Patent: Oct. 14, 1997

[54] PROCESS FOR PERFORMING RETRO-ALDOL REACTION

[75] Inventor: Michael J. Rodriguez, Indianapolis, Ind.

[73] Assignee: Eli Lilly and Company, Indianapolis, Ind.

[21] Appl. No.: 763,584

[22] Filed: Dec. 10, 1996

Related U.S. Application Data

[63] Continuation of Ser. No. 339,525, Nov. 15, 1994, abandoned.

[51] Int. Cl.$^6$ .................... C07K 1/107; C07C 67/47
[52] U.S. Cl. .................... 530/345; 530/317; 530/402; 530/406; 530/300; 568/308; 568/414; 562/463; 562/577; 560/53; 560/17.1; 564/169; 564/199; 561/443; 561/502
[58] Field of Search ............... 530/345, 317, 530/300, 402, 406; 568/308, 414; 562/463, 577; 560/53, 17.1; 564/169, 199; 561/443, 502

[56] References Cited

U.S. PATENT DOCUMENTS

| | | | |
|---|---|---|---|
| 5,057,493 | 10/1991 | Takesako et al. | 514/11 |
| 5,059,540 | 10/1991 | Bailey | 436/89 |
| 5,158,876 | 10/1992 | Takesako et al. | 435/71.1 |
| 5,200,505 | 4/1993 | Takesako et al. | 530/323 |
| 5,260,214 | 11/1993 | Takesako et al. | 435/254.1 |

FOREIGN PATENT DOCUMENTS

| | | |
|---|---|---|
| 0 352 092 | 7/1989 | European Pat. Off. . |
| 0 443 719 | 1/1991 | European Pat. Off. . |
| 0 510 271 | 4/1991 | European Pat. Off. . |
| 0 581 429 | 6/1993 | European Pat. Off. . |

OTHER PUBLICATIONS

*J. Org. Chem.*, 1981, 46, 4789–4791.
*J. Antibiotics*, Sep. 1991, vol. 44, No. 9, 925–933.
*J. Antibiotics*, Sep. 1991, vol. 44, No. 9, 919–924.
*J. Molecular Structure* (Theochem), 180 (1988) 383–387.

*Primary Examiner*—Ponnathapura Achutamurthy
*Assistant Examiner*—T. D. Wessendorf
*Attorney, Agent, or Firm*—Daniel W. Collins; Paul R. Cantrell; David E. Boone

[57] ABSTRACT

A process for removing β-hydroxy groups from β-hydroxy-containing compounds is disclosed. The process involves the use of a retro-aldol-promoting reagent selected from the group of trimethylamine-N-oxide, triethylamine-N-oxide, trimethylamine-N-oxide-hydrate, and trimethylamine-hydrate and requires dissolution of the substrate in an aprotic solvent and reaction under elevated temperatures. The process is broadly applicable to a variety of substrates including complex cyclic peptides, linear peptides, and non-peptides.

12 Claims, No Drawings

PROCESS FOR PERFORMING RETRO-ALDOL REACTION

This application is a continuation of application Ser. No. 08/339,525, filed on Nov. 15, 1994, abandoned.

BACKGROUND OF THE INVENTION

The current invention relates to a novel process for performing a retro-aldol reaction wherein a β-hydroxy group is removed from a variety of β-hydroxy-containing compounds, particularly peptides. This process is much more efficient than previously described processes, increasing the yield and purity of the desired product, and eliminating unwanted side-reactions and side-products. The current invention also allows for the selective removal of β-hydroxy groups when more than one such group is present. Further, the mild nature of the current retro-aldol-promoting reagents tolerates the presence of other functional groups on the substrates, such as, for example, ester and lactone bonds.

In the context of complex cyclic peptides, previously described methods for such reactions typically used strong bases acting as catalysts to remove β-hydroxy groups. For example, Takesako et al., U.S. Pat. No. 5,200,505, and Ikai et al., J. Antibiotics 44:925 (1991), describe the conversion of β-hydroxy-N-methylvaline and β-hydroxy-N-methylphenylalanine, amino acid residues on a complex cyclic peptide that had been produced by fermentation of certain Aureobasidium strains, to N-methylglycine using NaOH as catalyst.

Other methods to prepare non-hydroxy derivatives of these fermentation products entail a long and tedious total synthesis which has not proven practical (see European Patent Application 581429-A2; Karome, et al., "Total Synthesis of Aureobasidin A, An Antifungal Cyclic Depsipeptide", Presented at Peptide Symposium, Edmonton, Alberta, Canada, 1993).

Removal of β-hydroxy groups from non-peptide compounds has also been demonstrated in the art, again using strong bases acting as catalysts. For example, see March, Advanced Organic Chemistry, 3rd ed., John Wiley and Sons, New York, 1985, p. 831.

SUMMARY OF THE INVENTION

The current process stems from the discovery that trimethylamine-N-oxide (TNO) (Aldrich Chemical Company, Milwaukee, Wis.), triethylamine-N-oxide (ICN Biomedicals, Inc., Irvine, Calif.), trimethylamine-N-oxide-hydrate (TNO-hydrate) (Aldrich), and trimethylamine-hydrate (Aldrich), cause the removal of β-hydroxy groups from aldol compounds, which contain such groups. The reaction involved is characterized as a retro-aldol reaction according to the following general scheme:

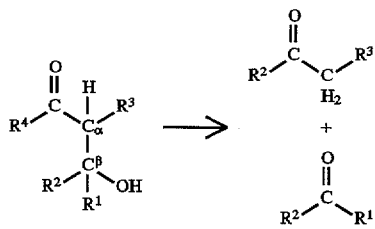

In particular, the current invention provides a process for removing β-hydroxy groups from a β-hydroxy-containing aldol substrate, comprising: heating the substrate in an aprotic solvent to between about 50° C. and about 100° C. in the presence of at least about 5 equivalents of a retro-aldol-promoting reagent selected from the group consisting of trimethylamine-N-oxide, triethylamine-N-oxide, trimethylamine-N-oxide-hydrate, and trimethylamine-hydrate.

DETAILED DESCRIPTION OF THE INVENTION

In the current invention, the term "aldol" indicates a molecule that is both an alcohol and an aldehyde or ketone wherein the hydroxyl and carbonyl functional groups are on adjacent carbon atoms as shown below. Thus, as used herein, the term "β-hydroxy group" refers to the alcohol moiety including both the β-carbon and the hydroxyl functional group that is resident on the β-carbon according to the following general structure:

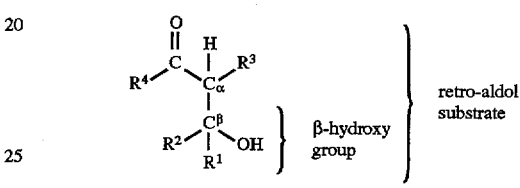

The use of this process for β-hydroxy group removal is broadly applicable to any compound having the aldol configuration. Preferred substrates include compounds wherein $R^1$ and $R^2$ are independently hydrogen, $C_1$–$C_8$ alkyl, $C_4$–$C_8$ cycloalkyl, phenyl, benzyl, naphthyl, or taken together with the carbon atom to which they are attached form a stable 4- to 7-membered hydrocarbon ring; $R^3$ is hydrogen, $C_1$–$C_8$ alkyl, $C_4$–$C_8$ cycloalkyl, phenyl, benzyl, naphthyl, acyl of the formula -C(O)R', carboxyl of the formula -C(O)OR', amino of the formula -N(R")R', amido of the formula -C(O)N(R")R', or peptidyl; $R^4$ is hydrogen, $C_1$–$C_8$ alkyl, $C_4$–$C_8$ cycloalkyl, phenyl, benzyl, naphthyl, -OR', or peptidyl; R' is hydrogen, $C_1$–$C_8$ alkyl, $C_4$–$C_8$ cycloalkyl, phenyl, benzyl, or naphthyl; and R" is hydrogen or methyl. Preferred compounds also include those wherein $R^3$ and $R^4$ taken together with the atoms to which they are attached form a cyclic peptide.

The term "alkyl" by itself or as part of another substituent, unless otherwise stated, includes saturated straight or branched aliphatic hydrocarbon radicals such as, for example, methyl, ethyl, n-propyl, isopropyl, n-butyl, sec-butyl, t-butyl, pentyl, hexyl, heptyl, octyl, nonyl, decyl, undecyl and dodecyl groups, and isomers and higher homologs of these radicals having the stated number of carbon atoms. Preferred alkyl groups are limited to 8 carbon atoms or less.

The term "cycloalkyl" refers to saturated ring structures having the stated number of carbon atoms such as cyclopropyl, cyclobutyl, cyclopentyl, cyclohexyl and cycloheptyl. Such cyclic structures are preferrably limited to 8 carbon atoms or less.

The term "acyl" refers to any group attached by means of the bivalent carbonyl radical. Such attached groups preferrably include hydrogen, alkyl, phenyl, and benzyl.

The term "peptide" or "peptidyl" is as commonly understood and indicates a compound or moiety comprising a sequence of amino acid residues. Peptides are generally distinguished by a covalent amide bond between a carbonyl group and an amino group. In addition, for purposes of this invention, peptides may include other types of bonds such as ester and lactone linkages. Peptides may be either cyclic or linear in nature. Thus, a β-hydroxy-containing peptide is a retro-aldol substrate of the structure above wherein $R^1$ and $R^2$ are as defined, and $R^3$ and $R^4$ comprise amino acid sequences attached to the aldol via ester or amide bonds. $R^3$ and $R^4$ may be linked together so as to form a cyclic peptide.

The term "hydrate" indicates the association of water molecules with the named reagent where the H-OH bond remains unbroken. Compounds often form more than one hydrate, i.e., differing numbers of water molecules may be associated with the reagents. References to hydrated reagents is understood to include all of the possible hydrate forms of the reagent.

The current invention provides a widely applicable process for the removal of β-hydroxy groups. Suitable substrates include complex cyclic peptides and linear peptides, hydrophilic or lipophilic peptides, and depsipeptides. Suitable substrates also include non-peptide compounds having the β-hydroxy functional groups. Thus, suitable substrates display a wide range in size, have differing solubilities in aprotic solvents, and may contain various sensitive functional groups such as, for example, carboxyl, amino, and hydroxyl.

Specific examples of suitable peptide substrates include members from a series of cyclic depsipeptides resulting from the fermentation of *Aureobasidium pullulans*. R106 factor 1 (hereinafter R106-1), the major product of the fermentation, has a β-hydroxy-containing residue whose β-hydroxy sidechain is readily removed by conditions of the current retro-aldol reaction without unwanted side-reactions, such as cleavage of the ester bond (see Example 1). At least seventeen other closely related factors (R106-2 through R106-18) have been isolated and identified (see U.S. Pat. No. 5,260,214; U.S. Pat. No. 5,158,876; U.S. Pat. No. 5,057,493; U.S. Pat. No. 5,200,505; Journal of Antibiotics, 44(9):925, 1991; Journal of Antibiotics 44(11):1187, 1991. These peptides are highly lipophilic.

Many of these natural products are antifungal agents. R106-1 is the most potent of the factors and is effective against a variety of clinically important fungal pathogens, such as *Candida albicans*.

Until recently, efforts to increase the potency of R106-1 and expand its spectrum have been limited due to the molecule's shortcoming of not having available chemical handles for modification. Moreover, efforts to generate chemical derivatives of these compounds through a total synthesis have been unsatisfactory. As shown in Reaction 1 below, when R106-1 is used as substrate retro-aldol cleavage produces an intermediate referred to as sarcosine having ready modification site for making derivatives.

Reaction 1:

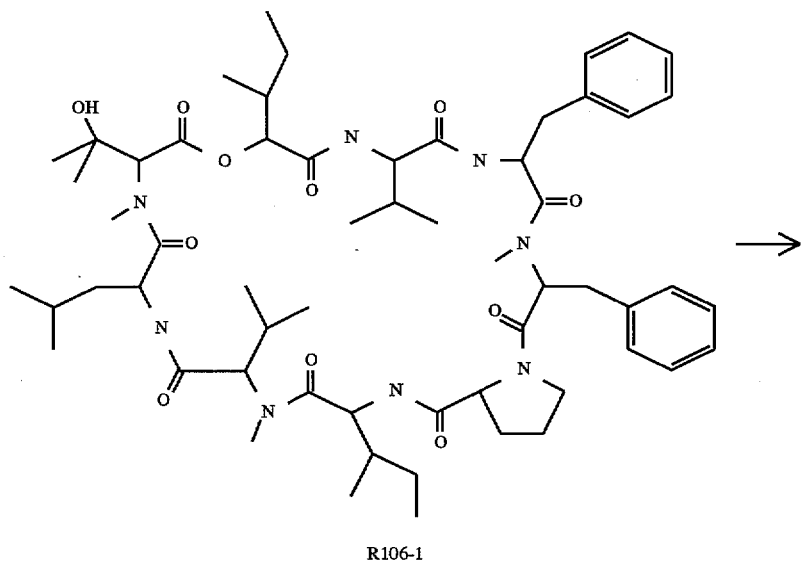

R106-1

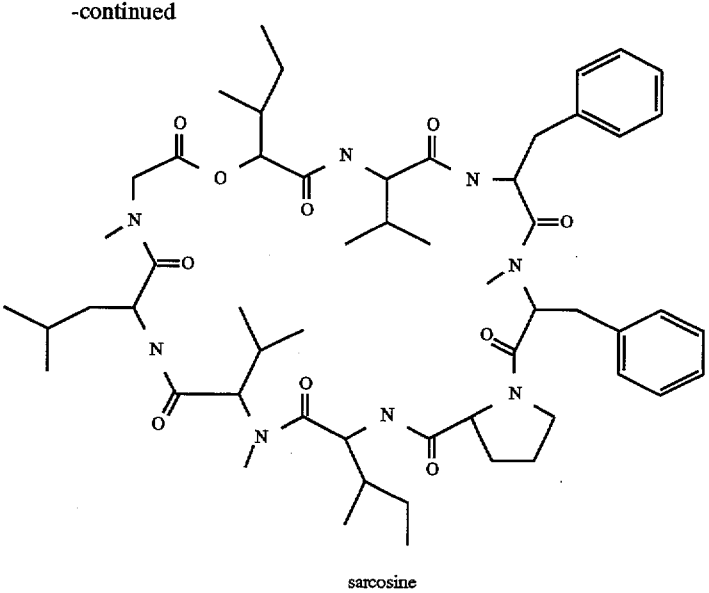

sarcosine

Limited yields of sarcosine can be generated using known catalytic reagents such as NaOH or KOH. However, since water in the reaction mixture will hydrolyze the ester bond, it is important to run these reactions under dry/inert conditions. Nevertheless, when reactions were conducted under these conditions, several by-products due to dehydration and hydrolysis were formed thereby reducing yields. In addition, much of the desired product was lost during work up.

In contrast, the retro-aldol-promoting reagents of the current process typically promoted yields of sarcosine under optimized conditions in excess of 92% with no major by-products (see Example 1).

Of course, compounds having the R106 nucleus that have previously been derivatized can likewise be reacted according to the current process.

The current process is also useful with other natural products. For example, a family of antifungal cyclic hexapeptides that is potent against a variety of opportunistic fungal pathogens such as *Candida albicans* serves as substrate for the retro-aldol reaction (see Example 3). These cyclic peptides are produced by culturing various microorganisms, a number of which are known in the art. Among these are echinocandin B, aculeacin, mulundocandin, sporiofungin, L-671,329, FR901379, and S31794/F1. All such antifungals are structurally characterized by a cyclic hexapeptide core, or nucleus, which contains an amino acid residue bearing a fatty acid acyl side chain. For example, echinocandin B has a linoleoyl side chain while aculeacin has a palmitoyl side chain. Thus, these cyclic hexapeptides differ from the R106 family of compounds by the fact that, while they have a polar nucleus, they also have a lipophilic sidechain.

Again, compounds of the echinocandin family that have previously been modified, but which retain a β-hydroxy group, also serve as retro-aldol substrates.

In addition, linear peptides having β-hydroxy groups also serve as substrates for the current reaction.

Non-peptides having β-hydroxy groups also serve as substrates for the current reaction (see Example 4). In such instances, the general requirements for β-hydroxy group removal are the same.

Exercise of the current invention requires addition of the substrate to an aprotic polar solvent, such as, for example, DMF, THF, acetonitrile, or DMSO. The use of acetonitrile, in particular, increases the purity of the desired product and is, therefore, preferred.

At least 5 eq (mole equivalents relative to the number of β-hydroxy groups resident on the substrate that are to be removed) of a retro-aldol-promoting reagent selected from the group consisting of trimethylamine-N-oxide, triethylamine-N-oxide, trimethylamine-N-oxide-hydrate, and trimethylamine-hydrate is added and the reaction can be run in a sealed tube or in a round bottom flask supplied with a water condenser. The addition of at least 10 eq of retro-aldol-promoting reagent substantially reduces the amount of byproducts and increases the reaction rate and is, therefore, preferred. Further, trimethylamine-N-oxide and trimethylamine-N-oxide-hydrate, in particular, facilitate higher yields and purity and are, therefore, preferred reagents for the current process.

Hydrated reagents generally lead to slower reaction times than when non-hydrated reagents are used, but the hydrated reagents typically increase the yield and purity of the retro-aldol product and are, therefore, preferred. Thus, trimethylamine-N-oxide-hydrate is a most preferred reagent for the current process.

After addition of the substrate and the retro-aldol-promoting reagent to an aprotic solvent, the reaction mixture is heated to between about 50° C. and about 100° C. for 3 to 72 hours. In general, increasing temperatures speed up reaction times. However, increased temperatures may have adverse effects on stability of the starting material. Thus, 70°–100° C. is the preferred temperature and 70° C. is most preferred.

When the retro-aldol reaction is catalyzed according to previously known methods by strong bases, such as NaOH, the presence of water in the reaction mixture has a significant detrimental effect on the yield obtained. In contrast, when using retro-aldol-promoting reagents of the current invention, yield and purity of the desired final product is essentially unaffected by water concentrations less than or equal to about 20%. However, at aqueous concentrations greater than about 20%, the reaction is incomplete after 2 days. Thus, the addition of between about 0% and about 20% water is preferred. When hydrated reagents are used, the further addition of about 0% water, such that the aqueous content of the reaction mixture results only from the hydrated reagents, is particularly preferred.

The scientific literature has described the decomposition of some amine-N-oxide reagents under thermal conditions. For example, trimethylamine-N-oxide was converted into trimethylamine and dimethylamine by heating marine samples at 100° C. for 1 hr or 120° C. for 30 minutes. Tokunage, T., Nippon Suisan Gakkaishi, 41(5):535–546, 1975. This raised the possibility that when amine-N-oxides were used as the retro-aldol-promoting reagent, trimethylamine was generated in situ and was the actual reagent responsible for the retro-aldol reaction. However, using commercially available trimethylamine as the reagent gave only starting material after several days at 70° C. (see Example 2, Table 1). Addition of water to trimethylamine indeed resulted in 33% sarcosine from R106-1 but by-products from dehydration and ester hydrolysis were detected by analytical high performance liquid chromatography (HPLC) as well, including high levels of olefin and open chain products. Thus, the use of trimethylamine as retro-aldol-promoting reagent requires the addition of water to the reaction mixture.

Where multiple β-hydroxy groups are present, reaction conditions of the current invention can be manipulated for selective removal of the β-hydroxy groups from the substrate. For example, R106-4, a factor in the fermentation products of *Aureobasidium pullalans*, contains both a β-hydroxy-valine and a β-hydroxy-phenylalanine residue as shown below. The concentration of the retro-aldol-promoting reagent was adjusted such that the β-hydroxy-phenylalanine was predominantly cleaved prior to removing the tertiary β-hydroxy group of the valine derivative. This result is contrasted to the use of NaOH/DMSO on R106-4, which, when used in amounts sufficient to initiate the reaction, catalytically removed both β-hydroxy groups from the starting compound. Of course, both β-hydroxy groups can be removed from R106-4 according to the current invention when increased amounts of retro-aldol-promoting reagents are included.

EXAMPLE 1

R106-1 (0.25 g, 0.22 mmol), obtained by fermentation from *Aureobasidium pullulans* as described in U.S. Pat. No. 5,057,493 (incorporated herein by reference), was dissolved in 2.5 ml acetonitrile and to this solution TNO-hydrate (0.25 g, 2.2 mmol) was added all at once. The reaction mixture was heated at 70° C. for 24 hr and then allowed to cool to room temperature after which the mixture was concentrated under vacuum to approximately one-half its original volume. The crude residue was dissolved in 200 ml ethyl acetate and washed with cold 10% HCl followed by saturated $NaHCO_3$ and brine. The organic layer was concentrated and the crude residue was purified by reverse phase preparative HPLC to yield 0.22 g of sarcosine (92%) as a white solid.

Fast atom bombardment mass spectrometry confirmed the molecular weight of the product having the chemical formula $C_{57}H_{87}N_8O_{10}$: calculated—1044.3; found—1043.7. Nuclear magnetic resonance (NMR) confirmed the disappearance of the two γ-methyl moieties associated with the β-hydroxy valine and registered the appearance of an additional α-proton in place of the removed β-hydroxy valine sidechain.

EXAMPLE 2

R106-1 was used as substrate as in Example 1 to further investigate the parameters of the retro-aldol reaction. Various reagents were tested under varying reaction conditions. Table 1 shows the effect of the varying conditions, identifying the specific reagents, solvents, time, and temperature employed. The relative amount of sarcosine product is shown in comparison to the amount of olefin impurity generated and unreacted starting material. Olefin impurity refers to the by-product produced by removal of the hydroxyl group only from the β-hydroxy alcohol moiety resulting in a double bond between the α- and β- carbons. Open ring by-product resulting from cleavage of the ester bond was also produced under some conditions where specifically noted in the table. HPLC conditions worked out in Example 1 were used to quantitate these ratios using sarcosine as a standard.

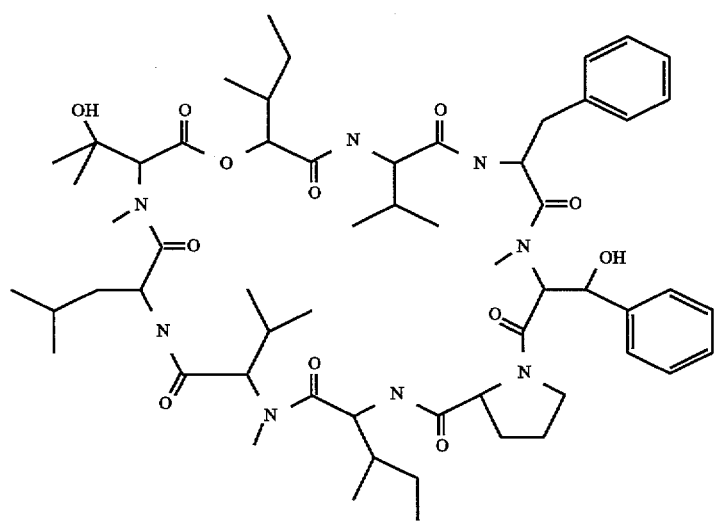

R106-4

As alluded to previously, temperature and time can also be manipulated to affect the speed and extent of β-hydroxy group removal.

In order that the invention described herein may be more fully understood, the following examples are set forth. It should be understood that the examples are for illustrative purposes only and are not to be construed as limiting the scope of the invention.

TABLE 1

| Reagent | eq | Solvent | Temp (C) | Rxn time | % Sarcosine/Olefin/R106 |
|---|---|---|---|---|---|
| none | — | DMF | 70 | 3 days | 0/0/100 |
| none | — | DMSO | 70 | 1 day | 0/0/100 |
| TNO · 2H$_2$O | 10 | DMF | 22 | 2 days | 0/0/100 |
| TNO · 2H$_2$O | 10 | DMF/H$_2$O(4:1) | 50 | 17 hrs | 0/0/100 |
| TNO · 2H$_2$O | 5 | DMF | 70 | 1 day | 55/25/20 |
| TNO · 2H$_2$O | 10 | DMF | 70 | 1 day | 82/18/0 |
| TNO · 2H$_2$O | 50 | DMF | 70 | 1 day | 79/21/0 |
| TNO · 2H$_2$O | 50 | DMF | 100 | 3 hrs | 70/30/0 |
| TNO · 2H$_2$O | 50 | DMF/H$_2$O (4:1) | 80 | 2 days | 83/17/0 |
| TNO · 2H$_2$O | 50 | DMF/H$_2$O(2:1) | 80 | 2 days | 40/13/47 |
| TNO · 2H$_2$O | 10 | DMF/H$_2$O(7:0.1) | 70 | 1 day | 88/12/0 |
| TNO · 2H$_2$O | 10 | ACN | 70 | 18 hrs | 93/7/0 |
| TNO · 2H$_2$O | 10 | THF | 70 | 1 day | 0/7/93 |
| TNO · 2H$_2$O | 10 | CH$_2$Cl$_2$ | 70 | 1 day | 0/0/100 |
| TNO (anhydrous) | 50 | DMF | 70 | 1 day | 65/35/0 |
| PNO | 10 | DMF | 70 | o.n. | 0/0/100 |
| NMO | 10 | DMF | 70 | o.n. | 0/trace/0 |
| TEA | 10 | DMF | 70 | o.n. | 0/0/100 |
| TEA | 10 | DMF/H$_2$O | 70 | 4 days | 0/trace/0 and open ring material |
| NaH | — | DMF | 22 | 1-2 hrs | open ring material |
| KBuO | — | DMSO | 22 | 3 hrs | 58/2/0 and open ring material |
| TMA | — | NEAT | 70 | days | 0/0/100 |
| TMA | 10 ml 25% aq | | 70 | o.n. | 24/71/5 |

PNO - pyridine N-oxide
NMO - N-methyl morpholine N-oxide
TEA - triethylamine
TMA - trimethylamine
KBuO - potassium t-butoxide
ACN - acetonitrile
DMF - dimethylformamide
DMSO - dimethylsulfoxide
o.n. - overnight run

EXAMPLE 3

An echinochandin molecule (320 mg, 0.288 mmol) having two threonine residues and a β-hydroxy-homotyrosine residue on the cyclic peptide as shown below, was dissolved in a mixture of acetonitrile and DMF (1:1). TNO-hydrate (1.6 g, 14.3 mmol) was added to the solution all at once. The reaction mixture was heated at 100° C. for 48 hr after which the mixture was cooled to room temperature and concentrated to approximately one-half its original volume. The crude residue was dissolved with acetic acid and purified by reverse phase preparative HPLC to yield 150 mg final product (52%). TNO-hydrate converted the two threonine residues into glycine residues and left the homotyrosine untouched as confirmed by fast atom bombardment mass spectrometry, which confirmed the molecular weight of the product having the chemical formula $C_{54}H_{65}N_7O_{13}$: calculated—1020.1; found—1020.8.

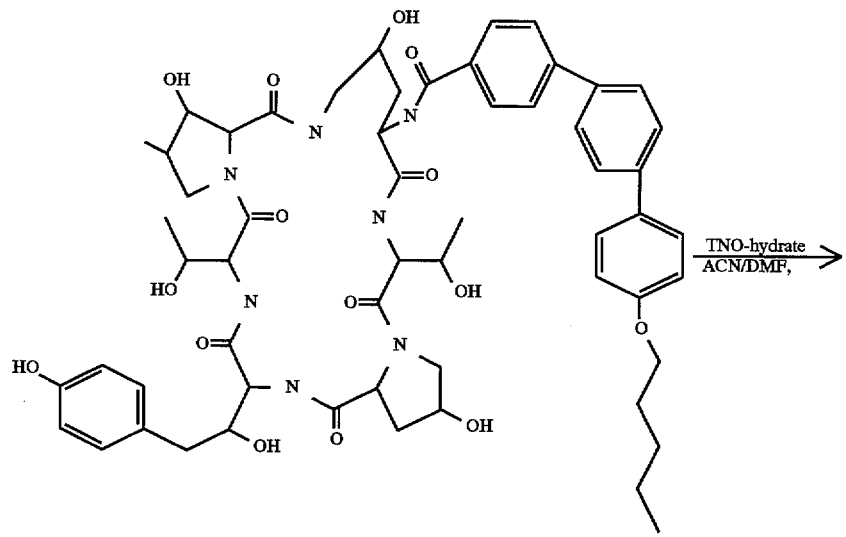

-continued

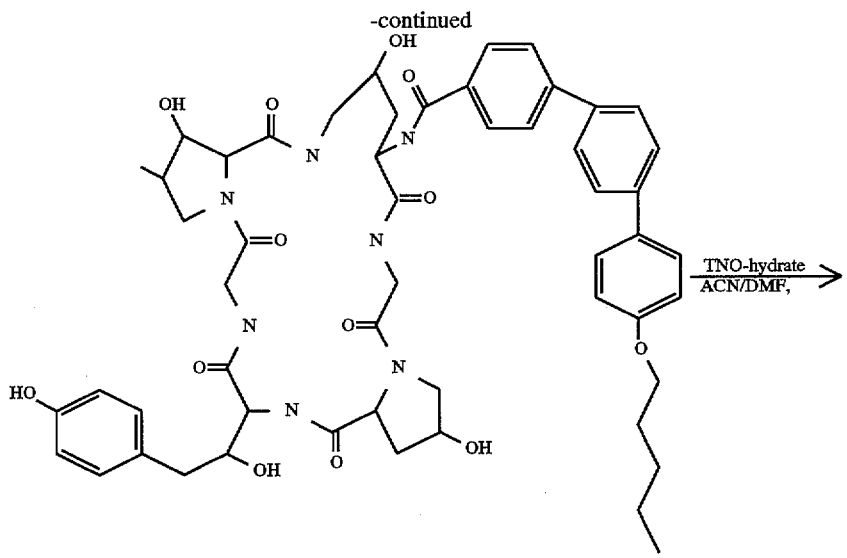

EXAMPLE 4

TNO-hydrate was used to promote a retro-aldol reaction on an alkyl ester derivative of ethylphenyl β-(dimethylhydroxy)acetate as shown below. The alcohol (0.5 g, 2.2 mmol) was suspended in 20 ml acetonitrile and to this solution was added all at once TNO-hydrate (2.5 g, 22.4 mmol). The reaction mixture was heated at 70° C. for 2 hr. The homogeneous solution was allowed to cool to room temperature and concentrated under vacuum to approximately one-half volume. The crude residue was dissolved in ethyl acetate, washed with cold 10% HCl followed by saturated NaHCO$_3$, and dried over Na$_2$SO$_4$. The organic layer was concentrated and the crude residue was purified by reverse phase preparative HPLC. The treatment removed the β-hydroxy group to yield acetone and 0.31 g (84%) of ethyl phenylacetate as confirmed by HPLC analysis with an authentic sample of ethyl phenylacetate. NMR confirmed removal of the β-hydroxy group and concomitant addition of an α-proton to the starting material.

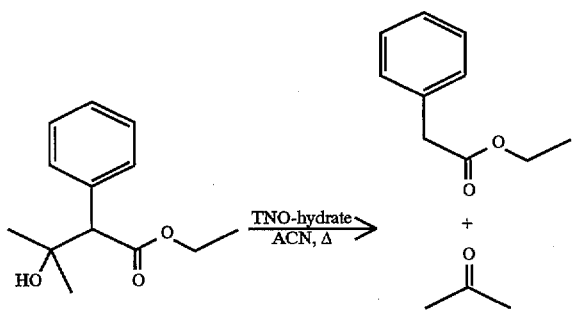

I claim:

1. A process for removing β-hydroxy groups from a β-hydroxy-containing substrate, comprising: heating the substrate in an aprotic solvent to between about 50° C. and about 100° C. in the presence of at least about 5 equivalents of a retro-aldol-promoting reagent selected from the group consisting of trimethylamine-N-oxide, triethylamine-N-oxide and, trimethylamine-N-oxide-hydrate.

2. The process of claim 1 wherein the β-hydroxy-containing substrate is a compound of the formula

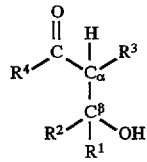

wherein R$^1$ and R$^2$ are independently hydrogen, C$_1$–C$_8$ alkyl, C$_4$–C$_8$ cycloalkyl, phenyl, benzyl, naphthyl, or taken together with the carbon atom to which they are attached form a stable 4- to 7-membered hydrocarbon ring; R$^3$ is hydrogen, C$_1$–C$_8$ alkyl, C$_4$–C$_8$ cycloalkyl, phenyl, benzyl, naphthyl, acyl of the formula -C(O)R', carboxyl of the formula -C(O)OR', amino of the formula -N(R")R', amido of the formula -C (O)N(R")R', or peptidyl; R$^4$ is hydrogen, C$_1$–C$_8$ alkyl, C$_4$–C$_8$ cycloalkyl, phenyl, benzyl, naphthyl, -OR', or peptidyl; R' is hydrogen, C$_1$–C$_8$ alkyl, C$_4$–C$_8$ cycloalkyl, phenyl, benzyl, or naphthyl; and R" is hydrogen or methyl.

3. The process of claim 2 wherein the β-hydroxy-containing substrate is a peptide.

4. The process of claim 2 wherein R$^3$ and R$^4$ taken together with the atoms to which they are attached form a cyclic peptide.

5. The process of claim 3 wherein the peptide is of the formula

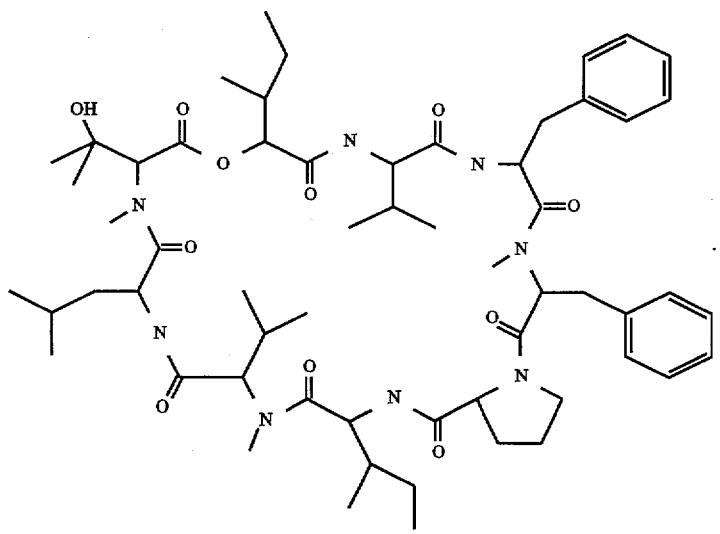

6. The process of claim 3 wherein the peptide is of the formula

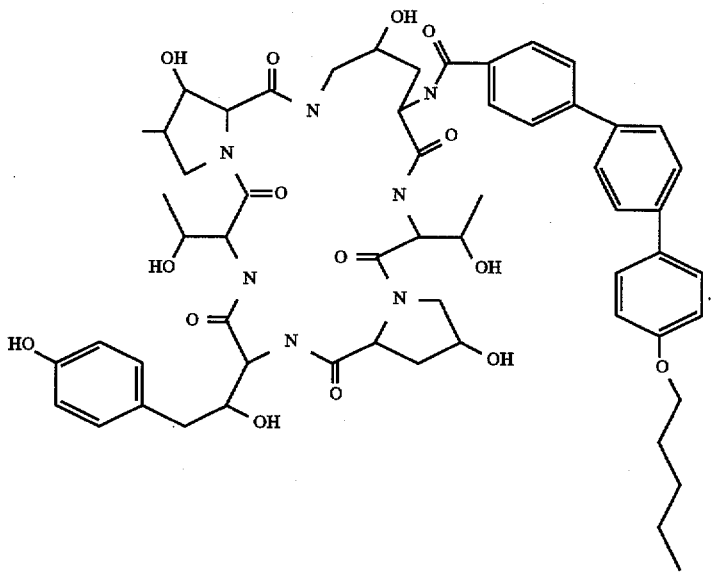

7. The process of claim 1 wherein at least 10 equivalents of the retro-aldol-promoting reagent are present.

8. The process of claim 1 wherein the retro-aldol-promoting reagent is trimethylamine-N-oxide-hydrate.

9. The process of claim 8 wherein the further added water content is about 0%.

10. The process of claim 1 wherein the reaction temperature is about 70° C.

11. The process of claim 1 wherein the water content is about 0% to about 20%.

12. The process of claim 1 wherein at least 10 equivalents of the retro-aldol-promoting reagent are present, the retro-aldol-promoting reagent is trimethylamine-N-oxide hydrate, the reaction temperature is about 70° C., and the further added water content is about 0%.

* * * * *

UNITED STATES PATENT AND TRADEMARK OFFICE
CERTIFICATE OF CORRECTION

PATENT NO. : 5,677,423

DATED : October 14, 1997

INVENTOR(S) : Michael J. Rodriguez

It is certified that error appears in the above-identified patent and that said Letters Patent is hereby corrected as shown below:

On the title page: Item [56] Reference Cited: U.S. Documents, last entry: "11/1993 Takesako et al." should read --01/1993 Takesako et al --.

Column 1, Line 58 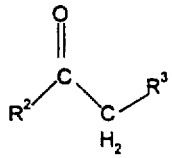 should read -- 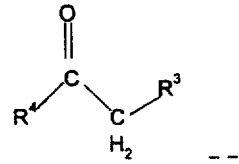 --

Column 7, Line 11 "generated in situ" should read -- generated *in situ* --

Column 12, Line 15  should be deleted.

Signed and Sealed this

Thirteenth Day of October 1998

Attest:

BRUCE LEHMAN

Attesting Officer

Commissioner of Patents and Trademarks